US007947024B2

(12) United States Patent
Ramage et al.

(10) Patent No.: US 7,947,024 B2

(45) Date of Patent: *May 24, 2011

(54) EMESIS CONTAINER

(75) Inventors: Richard F. Ramage, Laguna Beach, CA (US); Anthony F. Ramage, Ventura, CA (US); Richard B. Davies, Sandy, UT (US)

(73) Assignee: Richard F. Ramage and Anthony F. Ramage, Laguna Beach, CA (US)

( * ) Notice: Subject to any disclaimer, the term of this patent is extended or adjusted under 35 U.S.C. 154(b) by 527 days.

This patent is subject to a terminal disclaimer.

(21) Appl. No.: 12/005,451

(22) Filed: Dec. 27, 2007

(65) Prior Publication Data

US 2008/0221537 A1 Sep. 11, 2008

Related U.S. Application Data

(63) Continuation-in-part of application No. 11/714,949, filed on Mar. 7, 2007, now Pat. No. 7,686,791.

(51) Int. Cl.
*A61M 1/00* (2006.01)

(52) U.S. Cl. ........ 604/327; 604/317; 604/318; 604/322; 604/323; 604/325

(58) Field of Classification Search .................. 604/317, 604/318, 322, 323, 325, 327
See application file for complete search history.

(56) References Cited

U.S. PATENT DOCUMENTS

| | | | |
|---|---|---|---|
| 1,588,094 | A | 6/1926 | Chambers |
| 1,592,283 | A | 7/1926 | McKenzie |
| 1,597,556 | A | 8/1926 | Townsend |
| 1,692,951 | A | 11/1928 | Pinckney |
| 1,939,797 | A | 12/1933 | Swift |
| 2,323,287 | A | 7/1943 | Amberg |
| 2,374,153 | A | 4/1945 | Holtvoigt |
| 2,697,222 | A | 12/1954 | Reid |
| 2,943,660 | A | 7/1960 | Seeger |
| 2,948,936 | A | 8/1960 | Winthrop |
| 3,032,773 | A | 5/1962 | Piazze |
| D206,425 | S | 12/1966 | Faughnder |
| 3,578,236 | A | 5/1971 | Arai |
| 3,693,192 | A | 9/1972 | Knotts |

(Continued)

FOREIGN PATENT DOCUMENTS

WO WO 98/43593 10/1998

OTHER PUBLICATIONS

USPTO Office Action dated Jan. 18, 2008 regarding U.S. Appl. No. 11/714,949, 18 pages.

(Continued)

*Primary Examiner* — Tatyana Zalukaeva
*Assistant Examiner* — Ilya Y Treyger
(74) *Attorney, Agent, or Firm* — Ryan Kromholz & Manion, S.C.

(57) ABSTRACT

A collapsible, hands-free emesis container is provided with improved portability, deployment and emesis reception characteristics. The container includes a receptacle portion for receiving emesis, a chute portion for directing emesis and a retainer to maintain desired positioning of the container about a support structure, which may be the neck of an impaired patient. The container may be provided in a package having size characteristics for easy storage and access by emergency medical service personnel. The container may be formed as a single unitary member.

30 Claims, 11 Drawing Sheets

U.S. PATENT DOCUMENTS

| | | | |
|---|---|---|---|
| 3,797,734 | A | 3/1974 | Fleury et al. |
| 3,920,179 | A | 11/1975 | Hall |
| 3,945,048 | A | 3/1976 | Shearer |
| 4,169,472 | A | 10/1979 | Morris |
| 4,182,478 | A | 1/1980 | Etes |
| 4,233,688 | A | 11/1980 | Hjerl |
| 4,301,925 | A | 11/1981 | Bogart |
| 4,379,519 | A | 4/1983 | Sherwood |
| 4,598,458 | A | 7/1986 | McAllester |
| 4,610,039 | A | 9/1986 | Stern |
| 4,660,226 | A | 4/1987 | Quilling et al. |
| 4,838,327 | A | 6/1989 | Ambler et al. |
| 4,946,094 | A | 8/1990 | Stang |
| 4,990,145 | A | 2/1991 | Fleury |
| 5,056,932 | A | 10/1991 | Young |
| 5,062,558 | A | 11/1991 | Stang |
| 5,067,821 | A | 11/1991 | Young |
| 5,112,322 | A | 5/1992 | Hathaway |
| 5,133,085 | A | 7/1992 | de Pasquale Amicarelli et al. |
| 5,354,132 | A | 10/1994 | Young et al. |
| 5,356,398 | A | 10/1994 | Willis |
| 5,368,583 | A | 11/1994 | Fleury |
| 5,425,468 | A | 6/1995 | Birkel et al. |
| 5,599,332 | A | 2/1997 | Cashel |
| 5,647,670 | A | 7/1997 | Iscovich |
| 5,875,490 | A | 3/1999 | Woodard et al. |
| 5,971,969 | A | 10/1999 | Cashel |
| 6,016,772 | A | 1/2000 | Noyes |
| 6,024,094 | A | 2/2000 | Utecht |
| 6,070,277 | A | 6/2000 | Thomas |
| 6,074,376 | A * | 6/2000 | Mills ............................. 604/390 |
| 6,128,780 | A | 10/2000 | Reinhart et al. |
| 6,273,608 | B1 | 8/2001 | Ward, Jr. et al. |
| 6,554,810 | B1 | 4/2003 | Wilk et al. |
| 6,568,587 | B1 | 5/2003 | Yamada et al. |
| 6,589,220 | B2 | 7/2003 | Taylor |
| 6,602,230 | B1 | 8/2003 | Fisher et al. |
| 6,789,265 | B1 | 9/2004 | Vonrintein |
| 6,826,780 | B1 | 12/2004 | Romesburg |
| 6,874,936 | B2 | 4/2005 | Gillis et al. |
| 6,991,373 | B2 | 1/2006 | Carr et al. |
| 7,029,463 | B1 | 4/2006 | Estudillo |
| 7,041,042 | B2 | 5/2006 | Chertkow et al. |
| 2001/0054191 | A1 | 12/2001 | Frye |
| 2002/0095709 | A1 | 7/2002 | Fujikawa et al. |
| 2003/0009140 | A1 | 1/2003 | Taylor |
| 2004/0001653 | A1 | 1/2004 | Coval Carr et al. |
| 2005/0261644 | A1 | 11/2005 | Fields |
| 2007/0088299 | A1 | 4/2007 | Ayre |

OTHER PUBLICATIONS

USPTO Office Action dated Jul. 23, 2008 regarding U.S. Appl. No. 11/714,949, 24 pages.

USPTO Examiner Interview Summary dated Aug. 13, 2008 regarding U.S. Appl. No. 11/714,949, 4 pages.

USPTO Office Action dated Nov. 6, 2008 regarding U.S. Appl. No. 11/714,949, 25 pages.

USPTO Examiner Interview Summary dated Dec. 16, 2008 regarding U.S. Appl. No. 11/714,949, 4 pages.

USPTO Office Action dated Mar. 20, 2009 regarding U.S. Appl. No. 11/714,949, 18 pages.

USPTO Examiner Interview Summary dated Apr. 9, 2009 regarding U.S. Appl. No. 11/714,949, 4 pages.

USPTO Notice of Allowance and Interview Summary dated Aug. 26, 2009 regarding U.S. Appl. No. 11/714,949, 14 pages.

USPTO Advisory Action dated May 29, 2009 regarding U.S. Appl. No. 11/714,949, 4 pages.

* cited by examiner

EMESIS CONTAINER

RELATED APPLICATIONS

This application is a continuation-in-part of U.S. patent application Ser. No. 11/714,949, filed 7 Mar. 2007 now U.S. Pat. No. 7,686,791, and entitled "Emesis Container."

BACKGROUND OF THE INVENTION

The present invention relates generally to bodily fluid containment devices, and more specifically to a hands-free emesis container.

Emergency medical service (EMS) workers frequently encounter situations where a patient is unconscious, semi-conscious, altered, weak or otherwise impaired. The workers must act quickly to evaluate and stabilize the patient, set up IVs, prepare the patient for transport, communicate with hospital emergency staff, administer medications, and monitor and transport the patient to the hospital. These situations frequently involve patients who are vomiting or are on the verge of vomiting.

Emesis, or regurgitated contents of the stomach, is a medical treatment reality. Emesis further complicates emergency medical situations by distracting EMS workers from other important tasks. The workers suddenly find themselves juggling and holding traditional emesis basins or bags near the patient's face while simultaneously performing other lifesaving tasks, thereby reducing the multi-tasking efficiency of EMS workers. Despite a caregiver's best efforts, traditional emesis devices do not prevent patients from vomiting all over themselves while EMS workers are attending to other tasks.

In general, emesis containers are known in the art. These devices have several drawbacks, however. Most of the prior devices are not collapsible. An emesis container that is not collapsible may be suitable for some environments, but in an emergency medical situation, such configuration is inconvenient. If a collapsible container was provided in the past, it consisted of multiple pieces that required assembly prior to use. Such assembly simply subtracts precious seconds from attending to other medical needs in an emergency situation.

Additionally, prior devices did not address adequately the needs of a patient that is largely impaired. Most traditional emesis containers required, as previously noted, that the patient or caregiver support the container near the patient's mouth. While some devices offered supporting mechanisms, such as neckstraps, a minor patient head movement may remove the container from the flow path of the emesis, thereby allowing containment of only some of the fluid.

Therefore, the field of emergency medicine would benefit from a hands-free, collapsible emesis container with improved deployment and emesis reception characteristics.

SUMMARY OF THE INVENTION

The present invention provides a hands-free, collapsible emesis container with improved deployment and emesis reception characteristics.

The container is a unitary member comprised generally of a receptacle portion and a chute portion. The container may further comprise a retainer coupled to the container at retainer site. The receptacle portion is preferably a bag formed from a liquid impervious material, such as a translucent polyethylene, that may enable inspection of contents and may have volume demarcations thereon. The receptacle portion has an open end having a perimeter and a closed end. The chute portion has an entrance end and an exit end, the exit end being in fluid communication with the receptacle open end. The chute portion may extend around less than the entire receptacle open end perimeter. The chute is preferably a fluid impervious material and preferably includes a back panel, with a front surface and back surface, of substantial surface area and side panels extending from the bottom panel front surface. The junctions of the bottom panel and the side panels provide a fluid trough.

If a retainer is provided, the retainer may be coupled to the chute portion by being integrally formed with the chute portion. The retainer may be a strap, which may have elastic properties. Alternatively, or additionally, the retainer may include an adhesive patch, provided on the back surface covered by a releasable liner. The retainer site, at which the retainer is coupled to the container, may include a stress riser for ease in releasing the retainer. At least one retainer site may be an aperture formed through the chute portion. The retainer site may additionally or alternatively include a fastener, such as, e.g., a staple, for maintaining the retainer in frictional contact with the chute portion.

An emesis container according to the present invention may also include a reinforcement member coupled to the unitary member where the reinforcement member is adapted to maintain the open end of the receptacle portion in a substantially open configuration when the container is arranged for use. The reinforcement member may be coupled to an outer surface of the receptacle portion closer to the open end than to the closed end. The reinforcement member may be provided as a plastically deformable metal wire or even a cuff provided along at least a portion of the open end perimeter of the receptacle portion.

The exact dimensions of a container according to the present invention are not limiting. A preferred receptacle portion may have a liquid capacity of at least 1200 milliliters. The open end perimeter of the receptacle may encompass at least thirty square inches and the back panel front surface of the chute portion may comprise a surface area of at least forty square inches.

A container according to the present invention may be provided in a package surrounding and maintaining the emesis container in a folded configuration. The package may be airtight and have preferred dimensions of less than or equal to four inches long by less than or equal to four inches wide by less than or equal to one-half inch deep. The package may further contain instructions directed to the proper use of the container contained in the package.

Thus, although emesis always complicates an emergency situation, the availability of a hands-free emesis container will help considerably. Such availability is provided by a preferred method of packaging the container, which allows the emesis container to be carried easily by emergency personnel in their starter boxes, fanny packs, shirt pockets or glove holsters. Quickly attaching a hands-free emesis container to a patient will enable EMS workers to multi-task more efficiently without being distracted by holding traditional emesis containers near the face of an impaired patient. Attachment of the device to a patient is enabled by the retainer, which is preferably adapted to be situated around the patient's head or neck. With the aid of a chute having an increased surface area and curbed side sections, EMS workers can attend to other life-saving tasks, even when the patient is incapable of holding a conventional emesis container or substitute device, such as a trash can or bag.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
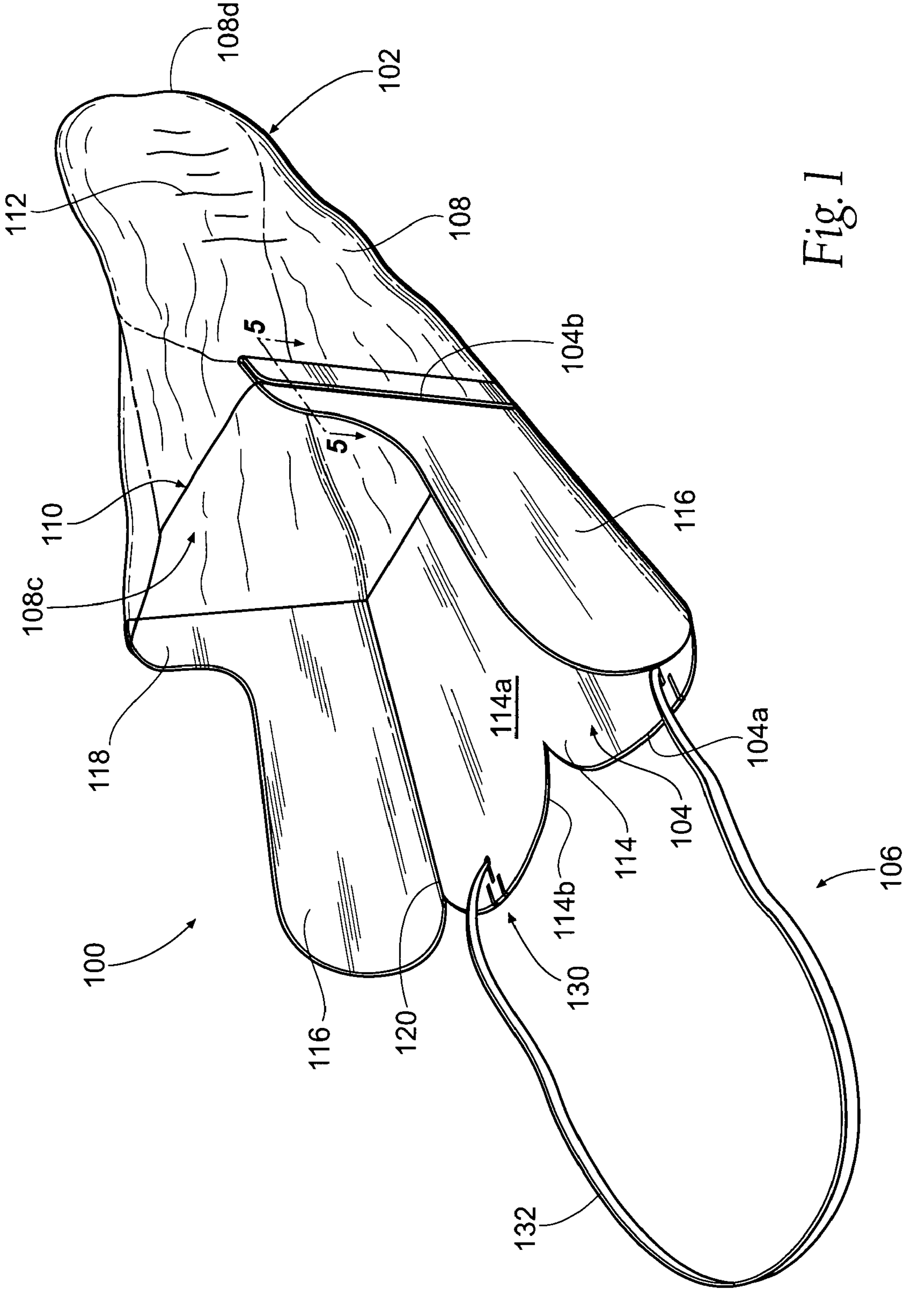
FIG. 1 is a perspective view of an embodiment of an emesis container according to the present invention.

Referring to FIG. 1, an embodiment of an improved emesis container 100 is shown. The container 100 includes a receptacle 102, a chute 104, and a retainer 106.

Figure 2:
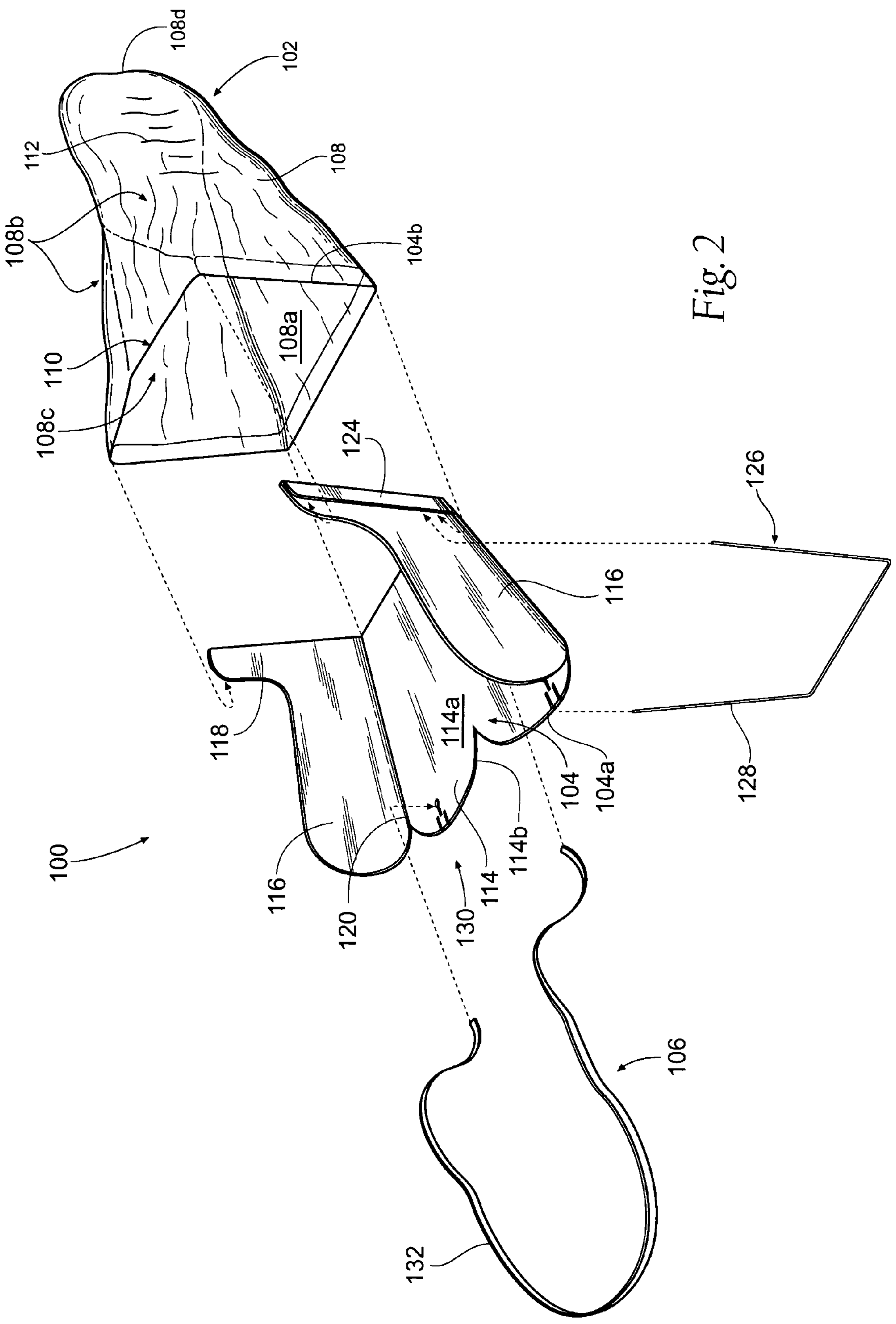
FIG. 2 is a perspective exploded view of the embodiment of FIG. 1.

With reference also to FIG. 2 the receptacle 102 is preferably in the form of a bag 108 having a back portion 108*a* and two side portions 108*b* extending between an open end 108*c* and a closed end 108*d*. The open end 108*c* of the bag 108 has a perimeter 110. The bag 108 is preferably formed from a flexible, liquid impervious material, such as polyethylene. While it should be understood that the receptacle 102 may be of any desirable size, a preferred bag has a capacity of at least 1200 milliliters of liquid. Furthermore, to aid in monitoring a patient's condition, the receptacle 102 may be provided with volume demarcations 112, which indicate the amount of liquid contained in the receptacle 102. In addition, the receptacle 102 may be formed of a material that is transparent or translucent to allow quick visual inspection of the container contents.

Figure 3B:
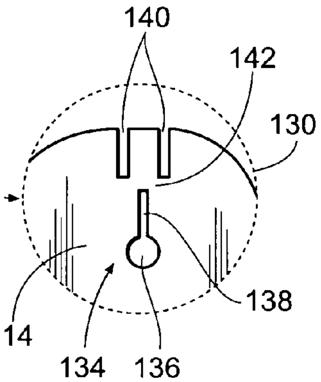
FIG. 3B is a close-up view of a retainer site on the chute of FIG. 3A.
Figure 3A:
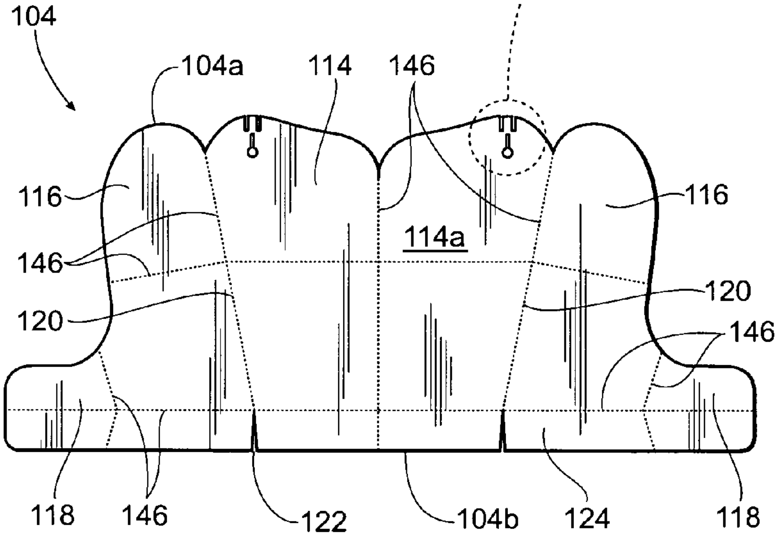
FIG. 3A is a front elevation view of an embodiment of an emesis chute according to the present invention.
Figure 3C:
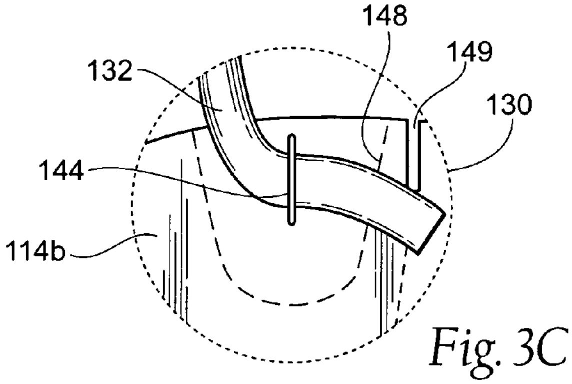
FIG. 3C is a close-up of an alternate retainer site.

Coupled to the receptacle 102 is the chute 104. Referring more specifically to FIGS. 3A-C, in addition to FIGS. 1 and 2, the chute 104 preferably comprises an entrance end 104*a* and an exit end 104*b*, with a back panel 114 and side panels 116 extending therebetween. The back panel 114 has a front surface 114*a* and a back surface 114*b*. The back panel front surface 114*a* is generally the receiving surface for emesis and, therefore, preferably has sufficient surface area to help collect the emesis. The preferred surface area comprises at least forty square inches. The side panels 116 preferably extend away from the back panel front surface 114*a*, perpendicularly or obliquely, along a panel junction 120, which may be provided as a score or crease 146. The side panels 116 may be formed integrally with the back panel 114 or attached thereto. To enable one method of assembly, the exit end 104*b* of the chute 104 is preferably formed with notches 122 proximate the panel junction 120. The chute 104 preferably includes an attachment margin 124 including and extending from the exit end 104*b* towards the entrance end 104*a*. The chute 104 preferably extends around less than the entire bag open end perimeter 110. The open end perimeter 110 preferably encompasses an area of at least thirty square inches. The chute 104 may be comprised of a material that is more rigid than the material comprising the receptacle 102. The added rigidity helps to maintain the receptacle 102 in a wide open configuration when the device 100 is in use.

To provide reinforcement that helps to maintain the receptacle 102 in an open configuration when the container 100 is in use, support tabs 118 are coupled to or formed integrally with the chute 104. While it is preferred that the chute 104 not extend around the entire bag open end perimeter 110 (see FIG. 1), the support tabs 118 may do so (not shown). To add further support to a coupling of the receptacle 102 and the chute 104, a reinforcement member 126 may be used. While various reinforcement members 126 will occur to those having skill in the art, the preferred reinforcement member 126 is a plastically deformable member such as a metal wire 128 or flat metal strip (not shown). The plastic deformability of the wire 128 aids in positioning and maintaining the open end 108*a* of the receptacle 102 in a desirable wide open configuration. Furthermore, the chute 104 may be provided with score lines 146, including the panel junctions 120, to aid in manufacturing, folding and packaging the container 100. A plurality of reinforcement members could also be used, such as foldable L- or U-shaped channel reinforcement structures (not shown) arranged over and supporting predetermined score lines 146.

To provide hands-free emesis collection by the container 100, a retainer 106 is provided, which is coupled to the chute 104 at retainer sites 130. While the retainer 106 may take many forms, the retainer 106 preferably comprises a flat strap 132. As seen in FIGS. 3A and 3B, a first preferred retainer site 130 comprises an aperture 134 having a hole 136 and a slot 138, and notches 140 cooperating with the aperture 134 to create a stress riser 142. The shape of the hole 136 is not specific or limiting. Rather, the hole 136 provides an area of less frictional resistance—than the slot 138—between the chute 104 and the retainer 106. A second preferred retainer site 130 is provided in FIG. 3C. In this embodiment, the retainer 106 is a flat strap 132 held in slidable, frictional contact with the chute 104 by a staple 144. In this embodiment, the frictional resistance between the chute 104 and the retainer 106 is kept relatively constant. With an appropriate choice of retainer 106, however, such as a strap 132 having elastic properties, when the retainer 106 is stretched, the friction lessens, enabling adjustment of the retainer 106 in the direction of the application of the stretching force. About the staple 144, perforations 148 may be provided, thereby creating at least one stress riser to enable tearing or removal of a portion the chute material for a quick disconnect of the device 100 from a patient or other support. Further, if a staple 144 is used to maintain the strap 132 in contact with the chute 104, the ends of the strap 132 may be provided with an inelastic portion or obstruction, such as a knot or aglet (not shown), that would prevent slippage through the staple 144, thereby preventing accidental removal of the strap 132 from the retainer site 122. In addition, an additional friction fit slot 149 may be provided in addition to the staple 144 to further reinforce the coupling of the retainer 106 to the chute 104.

Turning now to FIGS. 4A-D, a preferred method of assembling an embodiment of an emesis container according to the present invention includes forming the receptacle 102, the chute 104 and the retainer 106, and then coupling the components together. The receptacle 102 is formed from raw materials. For instance, where the receptacle 102 is a bag 108, polyethylene sheet material may be used. The chute 104 may be formed from a material suitable for liquid exposure over a determinable time. For example, the chute 104 may comprise a paperboard material having at least one side coated with a liquid impervious wax or plastic coating. The retainer 106 may be a simple flat strap portion cut from a spool of material.

Figure 4A:
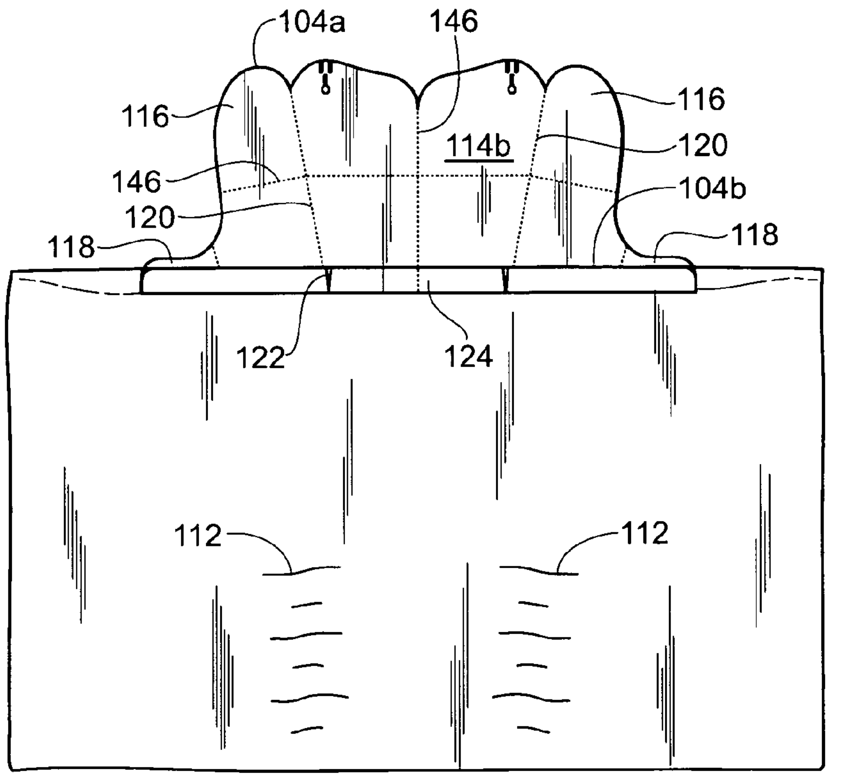
FIG. 4A is a front elevation view of a first assembly step in a first process for assembling the emesis container of FIG. 1.

After the receptacle raw material is selected and the chute 104 is formed, the coupling of the bag 108 to the chute 104 is achieved preferably through the use of a thermal bonding process including a thermal press or crimp. While the bag material could simply be thermally pressed to the chute attachment margin 124 or other attachment points, it is preferred that the attachment margin 124 be folded towards the chute back panel back surface 114*b* (as shown) or folded towards the chute back panel front surface 114*a* (not shown). Into the fold, the material to comprise the bag 108 may be inserted and then heat bonded to both the chute attachment margin 124 and the chute back surface 104*b*. The sheet material is then folded over the attachment margin 124, as is shown in FIG. 4A.

Figure 4B:
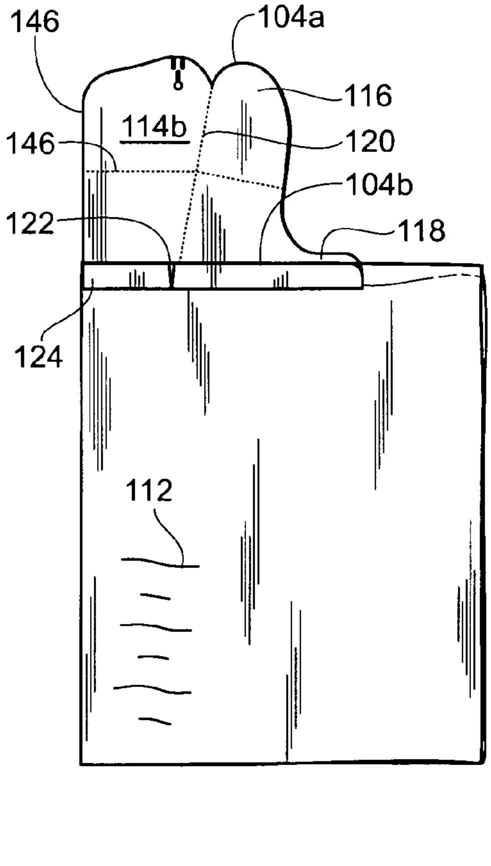
FIG. 4B is a front elevation view of a second assembly step in the first process for assembling the emesis container of FIG. 1.
Figure 4C:
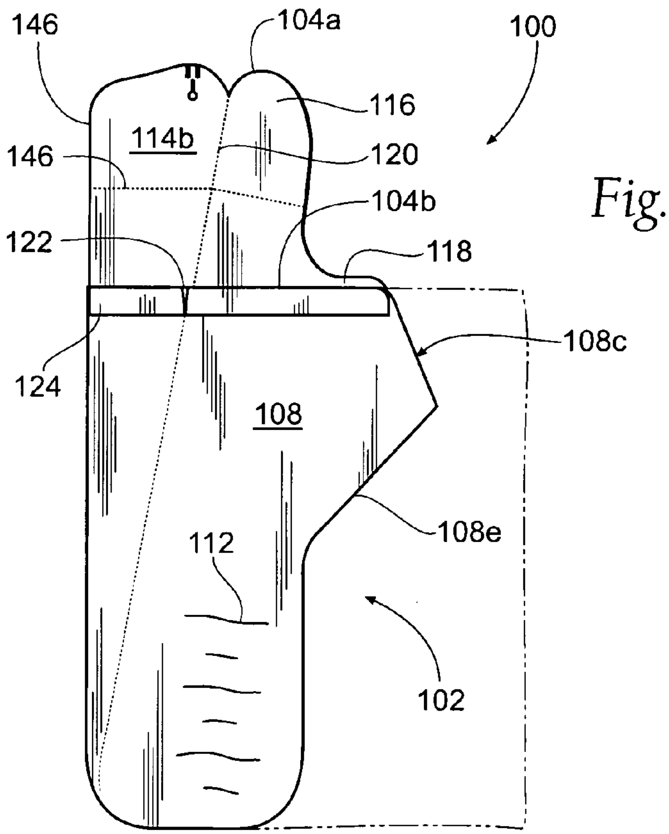
FIG. 4C is a front elevation view of a third assembly step in the first process for assembling the emesis container of FIG. 1.
Figure 4D:
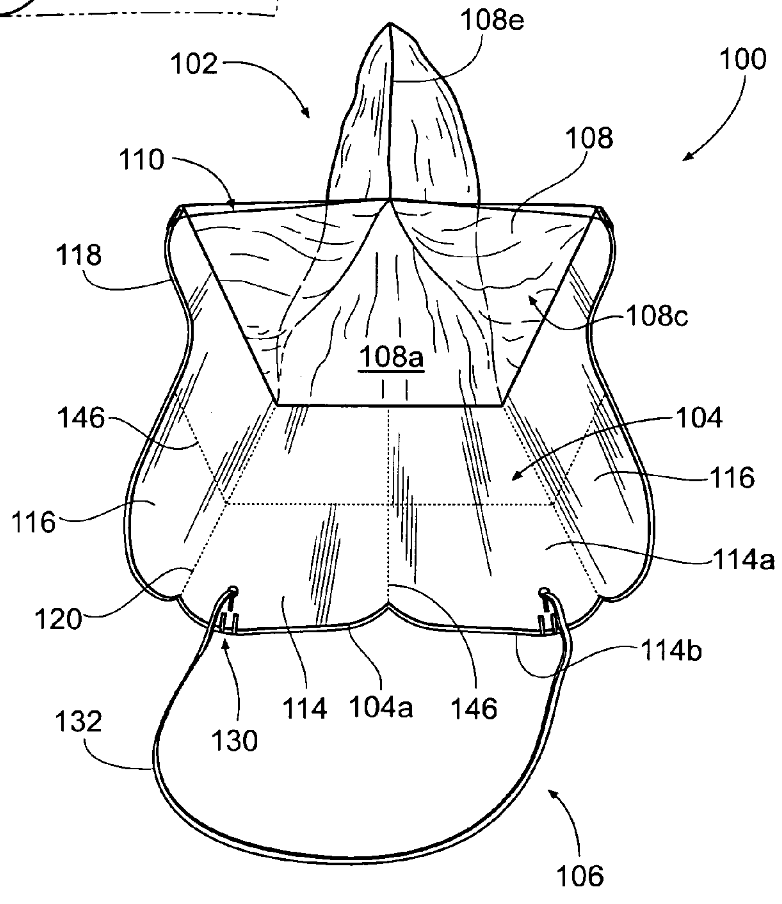
FIG. 4D is a top perspective view of the embodiment of FIG. 1.
Figure 5:
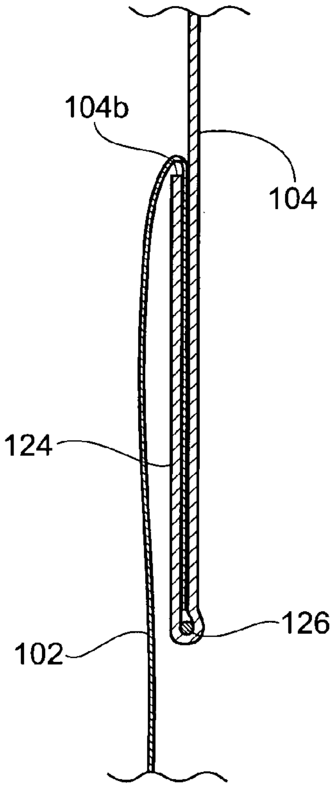
FIG. 5 is a partial cross-section view taken along line 5-5 in FIG. 1.

After the bag material has been heat sealed to the chute 104, the chute 104 may be folded along a medial score 146, thereby causing the sheet material to fold too, as seen in FIG. 4B. A formed joint can be seen in FIG. 5. A desired shape of the bag 108 may be obtained by using a heat sealer, such as an L-bar heat sealer or heated wire in a desired shape, to seal and trim the bag 108, as seen in FIG. 4C, along a front seam 108*e* and the closed end 108*d*, and excess material may be trimmed from the open end 108*c* of the bag 108.

Figure 6:
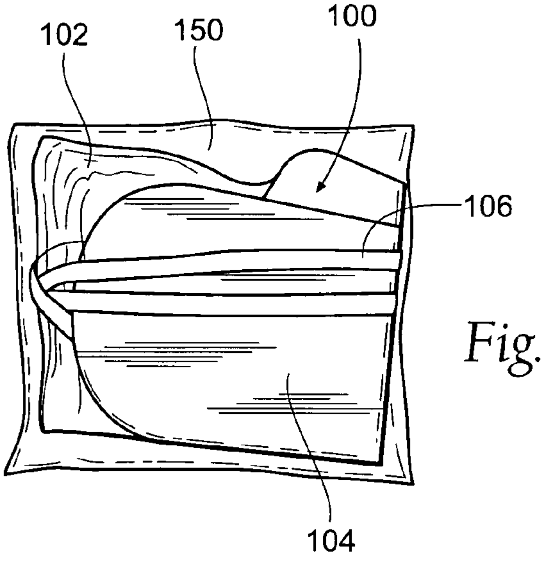
FIG. 6 is a top plan view of the embodiment of FIG. 1 in a folded and packaged configuration.

An emesis container according to the present invention is preferably packaged in a compact way that allows easy deployment by users in emergency medical situations, among others. The ease in deployment is facilitated by convenient packaging 150. As seen in FIG. 6, an emesis container 100 is folded in such a way to allow compact packaging. The folding may be aided by the scoring or creases 146 provided in the chute 104. The package 150 is preferably formed from a plastic sheet material as is well known. An emesis container 100 in a packaged configuration is preferably no larger than four inches long by four inches wide by one-half of an inch thick. Such a size enables convenient, easy storage of the devices.

While the emesis container was designed to be rather self-explanatory to use, the packaging 150 may further contain instructions (not shown) directed to proper use of the container 100, adjustment of the retainer 106, and proper disposal methods.

Figure 7:
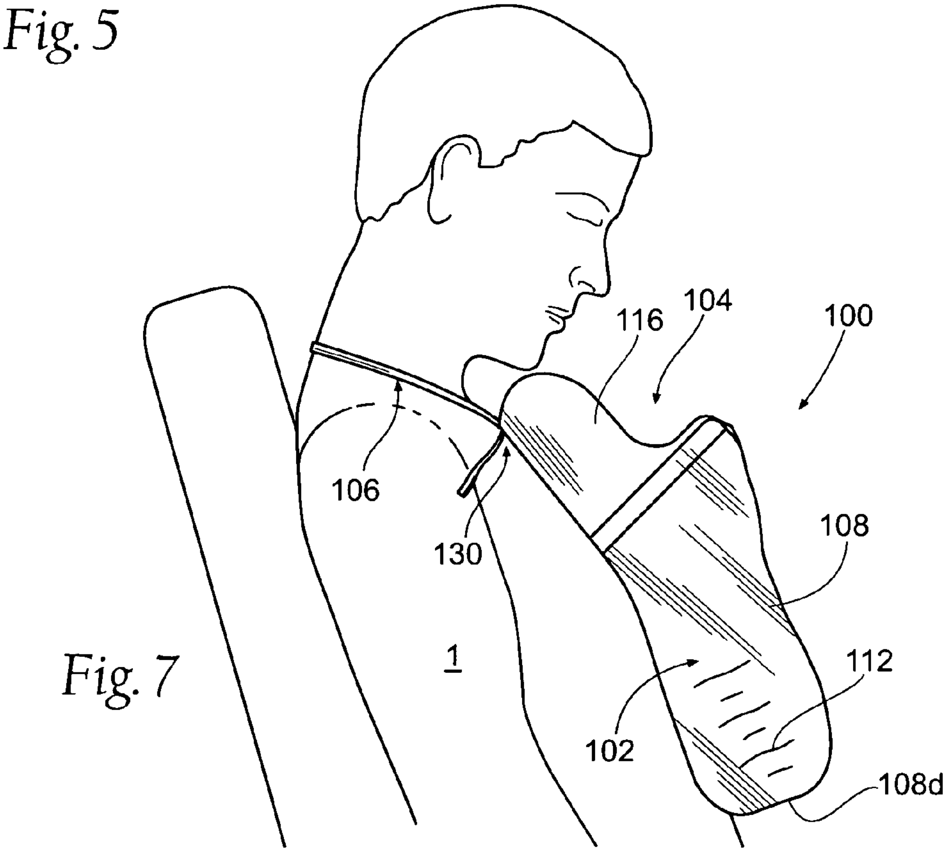
FIG. 7 is an anatomical right side elevation view of the embodiment of FIG. 1 in use.
Figure 8:
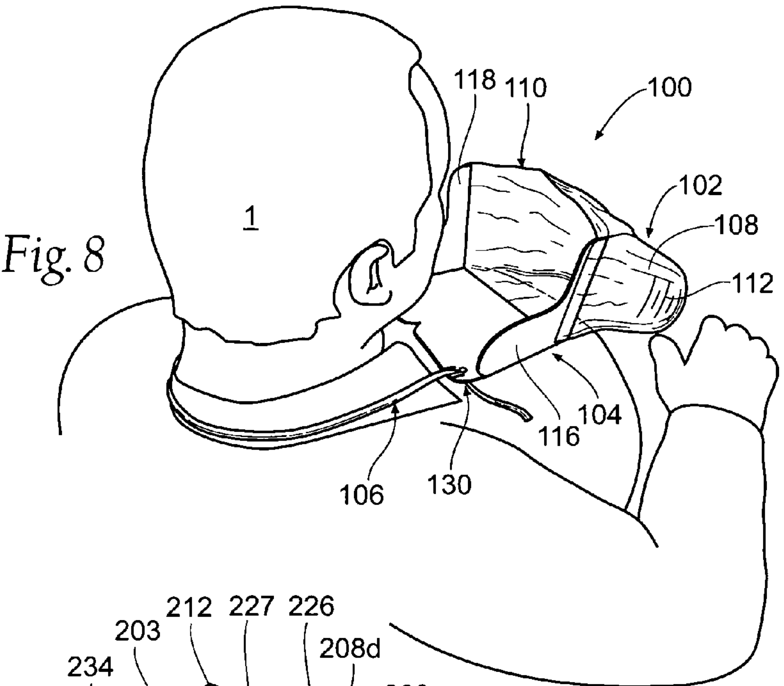
FIG. 8 is a top perspective view of the embodiment of FIG. 1 in use.

With reference to FIGS. 7 and 8, to use an emesis container according to the present invention, a user removes a container 100 from its package 150, unfolds the container 100, and places the retainer 106 about a support structure, such as the neck of the patient 1, to allow positioning of the chute 104 under the chin of the patient 1. The retainer 106 maintains proximity between the emesis container 100 and the mouth of the patient 1. Preferably, the patient 1 may be positioned in various poses and the retainer 106 will maintain such proximity, such as when the patient 1 is walking, standing, or sitting, or when the patient 1 is in a semi-Fowler's, a high-Fowler's, a left-lateral, or a right-lateral position. Indeed, the container 100 may even be used when the patient 1 is fitted with a cervical brace.

The retainer 106 is adjusted to provide proper positioning. Where the retainer 106 is a flat strap 132, the strap 132 may be adjusted a number of ways. While the strap 132 could be provided with an adjustment buckle, preferred adjustment is achieved by using the retainer site 130. If the strap 132 is kept in frictional contact with the chute 104 by a staple 144, the strap 132 may be pulled through the staple 144 to adjust positioning of the container 100.

A staple 144 may not work for some situations, however. For example, the retainer 106 may not be long enough to easily slip over a desired support structure. In such circumstances, the retainer 106 is preferably a flat strap 132 in cooperation with the chute 104 at a retainer site 130 having an aperture 134. The strap 132 can be removed from the site 130, threaded about a support member such as the neck of the patient 1, and threaded back through a hole 136 of the aperture 134 from which it was removed. While the strap 132 is in the hole 136, the strap 132 can move relatively freely through the aperture 134, thereby allowing easy adjustment. When desired positioning is achieved, the strap 132 can be forced into the slot 138 of the aperture 134. While the strap 132 is in the slot 138, a friction fit is provided, thereby maintaining the desired positioning.

To remove the container 100 from the patient 1, one method involves lifting or supporting the container 100 while removing the retainer 106 from the support structure. For instance, if the retainer 106 is a strap 132, the strap 132 may be lifted up and over the patient's head. Alternatively, the retainer 106 may be disconnected from one or both retainer sites 130. If the retainer 106 is a strap 132 coupled to the chute 104 by a staple 144, the strap 132 may be pulled out of the friction fit and the container 100 removed from the patient 1.

Alternatively, if a staple 144 is used, the retainer site 130 may be provided with the perforated section 148 to enable tearing or removal of a portion the chute material for a quick disconnect of the device 100 from a patient or other support upon the exertion of a determinable force. This method is preferred if the strap 132 includes an anti-slip mechanism, such as an aglet. In a similar fashion to using a strap 132 in combination with a staple 144, if the retainer 106 is a strap 132 in frictional cooperation with an aperture 134 at a retainer site 130, the strap 132 could be removed from the aperture 134; or the chute 104, itself, may be caused to fail at a stress riser 142 formed by the aperture 134 and cooperating notches 140. Once the container 100 is removed from the patient 1, the container 100 is simply disposed of, preferably by being thrown into a biohazard receptacle.

Figure 9A:
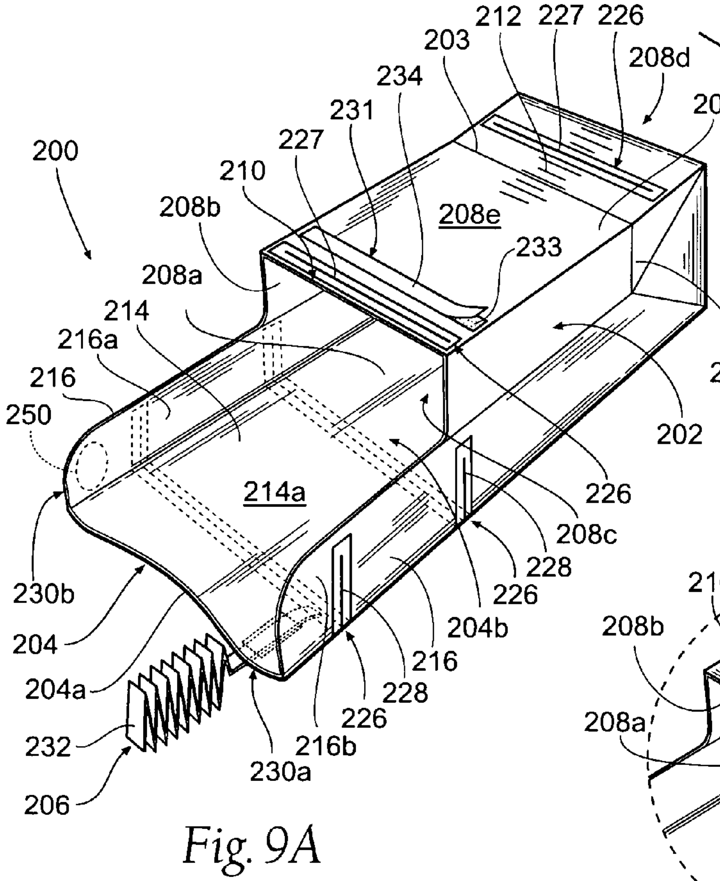
FIG. 9A is a perspective view of a second embodiment of the present invention.

A second embodiment 200 of an emesis container according to the present invention is a container 200 that is formed substantially or completely as a unitary member, which may be seamless about the circumference of its receptacle 202, as shown in FIG. 9A. Like the first embodiment 100, this embodiment 200 includes a receptacle 202, a chute 204, and preferably, though not necessarily, a retainer 206. The receptacle 202 is preferably in the form of a bag 208 having a back panel 208*a*, two side panels 208*b*, and a front panel 208*e* extending between an open end 208*c* and a closed end 208*d*. The front panel 208*e* may be provided with a crease 203 for collapsing the receptacle 202 into a planar configuration prior to use. The open end 208*c* of the bag 208 has a perimeter 210. The bag 208 is preferably formed from a flexible, liquid impervious material, such as polyethylene. While various material thicknesses may be employed, a preferred thickness is three to five mils, which is preferably substantially uniform throughout the unitary member. While it should be understood that the receptacle 202 may be of any desirable size, a preferred bag 208 has a capacity of at least 1200 milliliters of liquid. Furthermore, to aid in monitoring a patient's condition, the receptacle 202 may be provided with volume demarcations 212, which indicate the amount of liquid contained in the receptacle 202. In addition, the receptacle 202 may be formed of a material that is transparent or translucent to allow quick visual inspection of the container contents.

Coupled to the receptacle 202 is the chute 204. Such coupling is preferably provided by the chute 204 being integrally formed with the receptacle 202. The chute 204 preferably comprises an entrance end 204*a* and an exit end 204*b*, with a back panel 214 and side panels 216, each having a side panel front surface 216*a* and a side panel back surface 216*b*, extending at least partially therebetween. The back panel 214 has a front surface 214*a* and a back surface 214*b*. The back panel front surface 214*a* is generally the receiving surface for emesis and, therefore, preferably has sufficient surface area to help collect the emesis. The preferred surface area of the back panel front surface 214*a* comprises at least thirty-six square inches. The side panels 216 preferably extend away from the back panel front surface 214*a*, perpendicularly or obliquely. The side panels 216 are preferably formed integrally with the back panel 214. The chute 204 preferably extends around less than the entire bag open end perimeter 210. The open end perimeter 210 preferably encompasses an area of at least thirty square inches.

To provide hands-free emesis collection like the first embodiment 100, a retainer 206 is provided for the second embodiment 200, which is coupled to the chute 204 at retainer sites 230. While the retainer 206 may take many forms, the retainer 206 preferably comprises a flat strap 232. The strap 232 may be formed integrally with or otherwise coupled to the chute 204 at a first retainer site 230*a*, which is preferably provided towards the right side of the chute back panel 214. The strap 232 may be accordion folded for convenience in packaging and deployment. The strap 232 is preferably adapted to engage the left portion of the chute 204 at a second retainer site 230*b*, to form a loop. At the second retainer site 230*b*, a strap adhesive patch 250 is preferably provided on the outer surface 216*b* of the side panel 216 on the left side of the chute 204, the patch 250 being preferably protected by a removable liner (not shown). While various shapes would provide sufficient function, the strap adhesive patch 250 is preferably provided in the shape of a circle so as to provide substantially the same adhesive properties regardless of the application angle of the strap 232 to the patch 250. A preferred strap 232 is between and including one-half inch to one inch wide by twenty-two inches long.

Alternatively, the retainer 206 may be provided as a pair of flat straps formed integrally with, and extending from the entrance end 204*a* of the chute 204. Though two straps may be formed integrally with the container 200, they may, instead, be supplied separately from the container 200 and then coupled to the container 200. One of the straps may be provided with an adhesive patch protected by a removable adhesive shield. In this way, when the retainer 206 is placed about a wearer's neck or other supporting structure, the adhesive shield may be removed and one strap may be adhered to the other to maintain the container 200 in a desired position. Alternatively, both straps may be provided with an adhesive patch that may be secured to the other, to themselves in a looping relationship, or to an alternate support structure, such as a cervical collar.

The receptacle 202 may be integrally formed without a seam about its circumference such that there is a continuous and uniform construction throughout the panels 208*a*, 208*b*, and 208*e*. That is, the container 200 may be created from an extruded tubular member, rather than from a folded sheet, resulting in a receptacle 202 that is seamless about its circumference. The container 200 may be formed of a polymer material including ethylene and/or propylene. Pellets of the polymer may be melted into a working composite mixture at about two hundred degrees Celsius, along with some additive agents for coloring purposes, if desired. This heated molten compound may be placed in a die where an extrusion process forms an open-ended tubular receptacle as the compound flows into gaps between an extruding member and the die. The extrusion process may take place at a controlled pressure of, e.g., 450 Bar. This process creates an open-ended tubular member with a seamless perimeter. After the extruded tubular member is formed, folds and creases may be formed, which convert the tubular member into a desired shape, such as a substantially rectangular shaped collapsible parallelepiped that folds into a flattened configuration. This step may be preferably done in an automated setting wherein a machine is utilized to create the folds and creases.

Furthermore, portions of the tubular member may be removed to further alter the shape of the container 200. In the preferred embodiment 200, the chute 204 may be formed by cutting away undesired portions of the tubular member. The bottom 208*d* of the bag 208 is closed and sealed, preferably with a heat-press, at an edge of the tubular member to ensure that there can be no leakage through the bottom of the receptacle 202.

The second embodiment 200 may further include one or more reinforcement members 226, which may be adapted to form a preferred structural shape before use and provide reinforcement to maintain the open end 208*c* of the receptacle 202 in a substantially open configuration during use. One type of reinforcement member 226 may be a plastically deformable metal wire 227, such as that employed in commonly available twist ties, coupled to the bag 208, which may be coupled to the receptacle front panel 208*e* and provided along at least a portion of the width of and near or at the open end 208*c* of the bag 208. Additional reinforcement members 226 may also be used. For instance, a second wire 227 may be provided between the preferred bag crease 203 and the bottom 208*d* of the bag 208. Although the wires 227 are shown to extend along only the front panel 208*e* of the bag 208, the wires 227 may also extend onto the side panels 208*b* of the receptacle 202. Alternatively or additionally, similar reinforcement members (not shown) may be provided coupled to the chute back panel 214 or receptacle back panel 208*a*. Also, alternatively or additionally, another type of reinforcement member 226 may be a plastically deformable metal wire 228 coupled to the bag 208 that spans at least partially across the width of the chute back panel 214 or receptacle back panel 208*a* and extends at least partially across one or both of the chute side panels 216 or receptacle side panels 208*b*, respectively. If desired, the wire 228 may span the entire width of the chute back panel 214 or receptacle back panel 208*a* as shown.

Figure 9B:
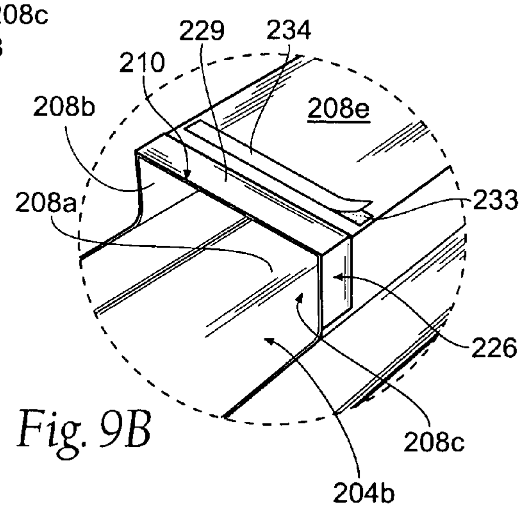
FIG. 9B is a perspective view of an alternate or additional reinforcement member to be used in conjunction with an embodiment of the invention.

Alternatively or additionally, as shown in FIG. 9B, the reinforcement member 226 may be a cuff 229 provided about a portion of the perimeter 210 of the open end 208*c*. One way of forming the cuff 228 may be to simply slit the sides 208*b* of the bag 208, thereby partially continuing a cut from a front edge of the chute side panels 216, and folding the material between the slits outward and towards the bottom 208*d* of the bag 208. Furthermore, the embodiment 200 may include a closure means 231, such as an adhesive patch 233 disposed on the front panel 208*e* of the bag 208. After use, the chute 204 may then be folded over the open end 208*c* of the bag 208 and adhered to the adhesive patch 233 after the selectively removable adhesive liner 234 has been removed. Another type of closure means that may be used is a plastically deformable wire (not shown), which may be coupled to the chute portion 204 near or at its entrance end 204*a*. In this way, after the container 200 has been used, the chute portion 204 may be folded over the open end 208*c* of the bag 208, and the wire used to secure the container 200 in a closed configuration for disposal or transport. An emesis container 200 may be provided in a packaged configuration that is preferably no larger than six inches long by three inches wide by one-half of an inch thick. Such a size enables convenient, easy storage of the devices.

Figure 10A:
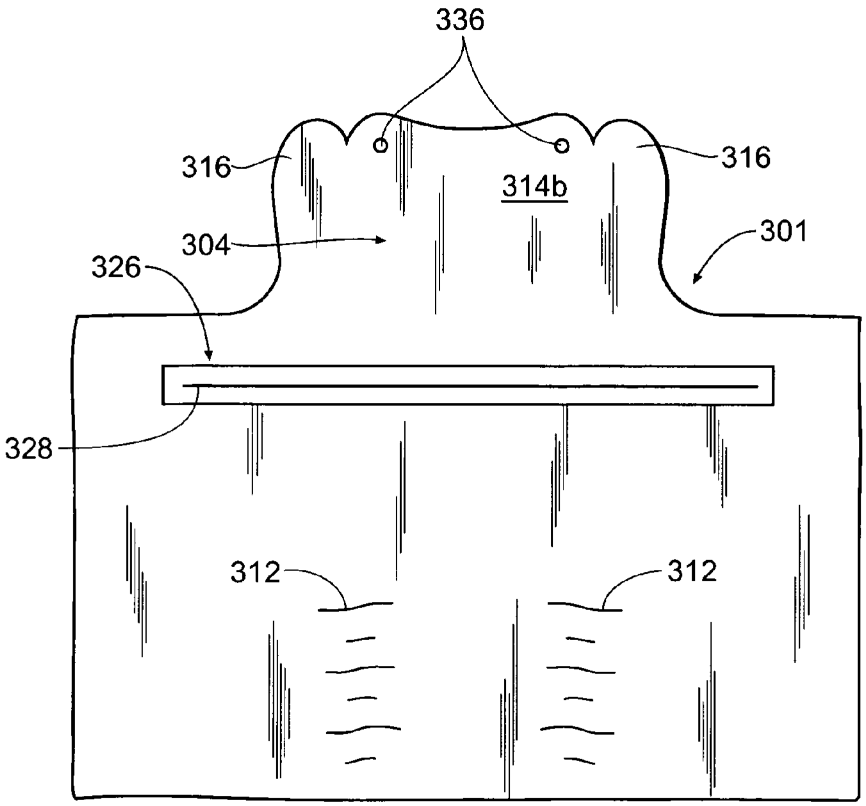
FIG. 10A is a back elevation view of a third embodiment of the present invention in a first assembly configuration.
Figure 10B:
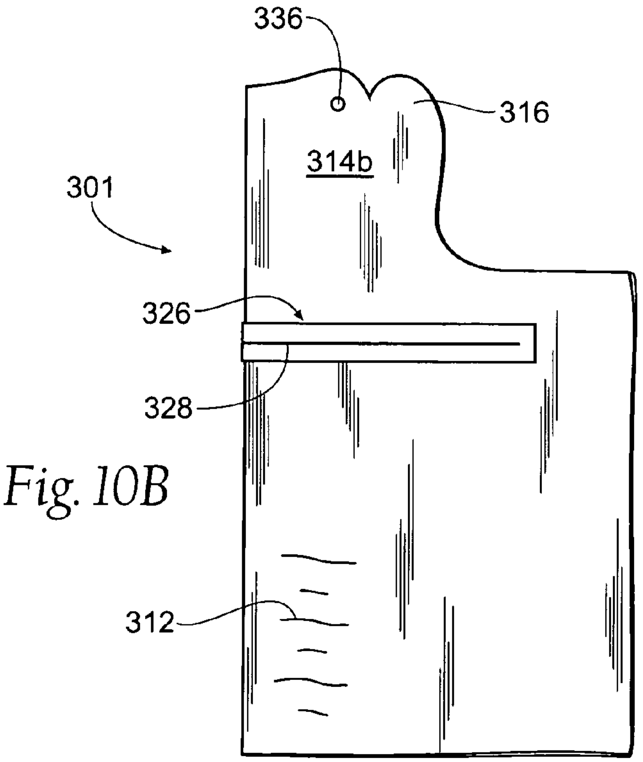
FIG. 10B is a right elevation view of the embodiment of FIG. 10A in a second assembly configuration.
Figure 10C:
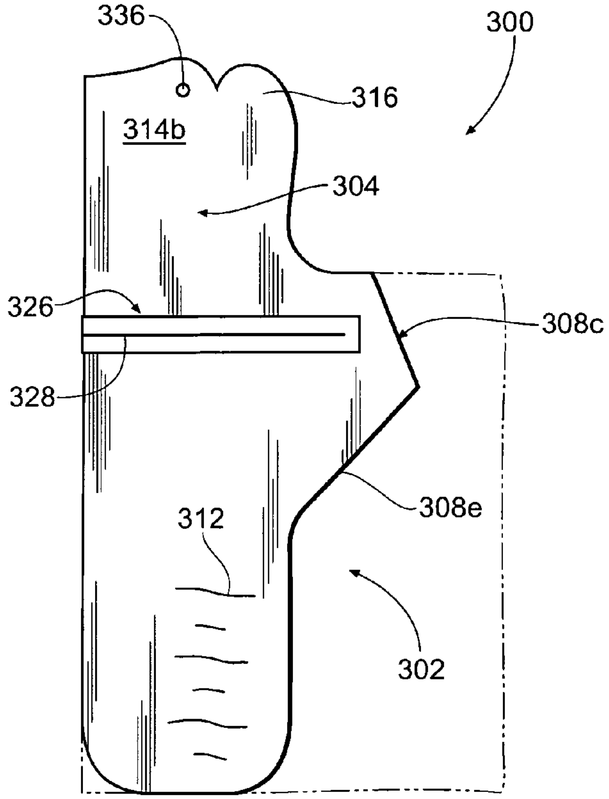
FIG. 10C is a right elevation view of the embodiment of FIG. 10A in a third assembly configuration.
Figure 10D:
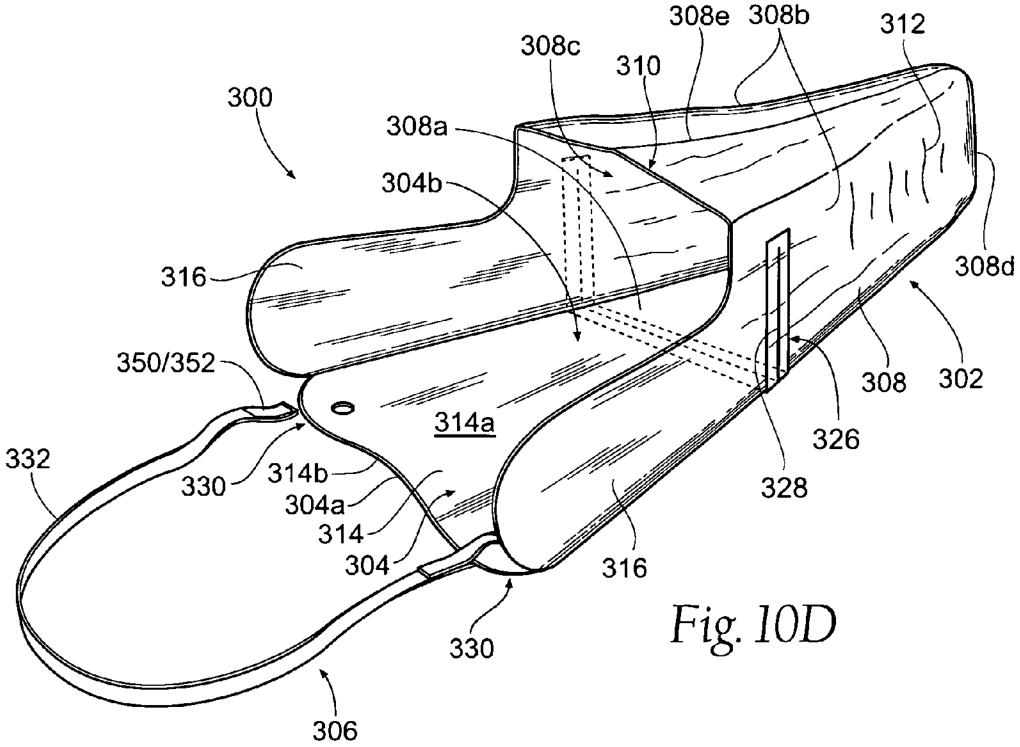
FIG. 10D is a perspective view of a completed container according to the third embodiment.

Yet another embodiment 300 of an emesis container according to the present invention may be a container 300 that is formed substantially or completely as a unitary member having a shaped form, as shown in FIGS. 10A-10D. This embodiment 300 may be formed from sheet material having been cut to a desired shape 301, such as in FIG. 10A, folded in half, as shown in FIG. 10B, and then sealed and trimmed, such as by way of a heated wire arranged in a desired shape. A sealed and trimmed container 300 is shown in FIG. 10C. Like the first embodiment 100, this embodiment 300 includes a receptacle 302, a chute 304, and preferably, though not necessarily, a retainer 306. The receptacle 302 is preferably in the form of a bag 308 having a back portion 308*a* and two side portions 308*b* extending between an open end 308*c* and a closed end 308*d*. The open end 308*c* of the bag 308 has a perimeter 310. The bag 308 is preferably formed from a flexible, liquid impervious material, such as polyethylene. While it should be understood that the receptacle 302 may be of any desirable size, a preferred bag 308 has a capacity of at least 1200 milliliters of liquid. Furthermore, to aid in monitoring a patient's condition, the receptacle 302 may be provided with volume demarcations 312, which indicate the amount of liquid contained in the receptacle 302. In addition, the receptacle 302 may be formed of a material that is transparent or translucent to allow quick visual inspection of the container contents.

Coupled to the receptacle 302 is the chute 304. Such coupling is preferably provided by the chute 304 being integrally formed with the receptacle 302. The chute 304 preferably comprises an entrance end 304*a* and an exit end 304*b*, with a back panel 314 and side panels 316 extending therebetween. The back panel 314 has a front surface 314*a* and a back surface 314*b*. The back panel front surface 314*a* is generally the receiving surface for emesis and, therefore, preferably has sufficient surface area to help collect the emesis. The preferred surface area comprises at least thirty-six square inches. The side panels 316 preferably extend away from the back panel front surface 314*a*, perpendicularly or obliquely. The side panels 316 may be formed integrally with the back panel 314 or attached thereto. The chute 304 preferably extends around less than the entire bag open end perimeter 310. The open end perimeter 310 preferably encompasses an area of at least thirty square inches.

To provide hands-free emesis collection like the first embodiment 100, a retainer 306 may be provided for the third embodiment 300, which is coupled to the chute 304 at retainer sites 330. While the retainer 306 may take many forms, the retainer 306 preferably comprises a flat strap 332 provided separately from, or formed integrally with, the chute 304. A first preferred retainer site 330 comprises a hole 336. The shape of the hole 336 is not specific or limiting. An end of the strap 332 may be provided with an adhesive patch 350 covered by an adhesive shield 352. In this way, when the retainer 306 is placed about a wearer's neck or other supporting structure, the strap 332 may be slid through the hole 336 located at the retainer site 330, the adhesive shield 352 may be removed and the strap 332 may be adhered to the chute 304 or even to itself 332 to maintain the container 300 in a desired position. Alternatively, both ends of the strap 332 may be provided with an adhesive patch 250 that may be secured to the chute 304, to themselves in a looping relationship, or to an alternate support structure, such as a cervical collar.

The third embodiment 300 may further include a reinforcement member 326 adapted to maintain the open end 308*c* of the bag 308 in an open configuration during use. Such reinforcement member 326 may be a plastically deformable metal wire 328, such as, e.g., a common twist tie that has been coupled to the receptacle portion 302 or the chute portion 304. The third embodiment 300 may also include reinforcement members similar or substantially identical to those discussed with reference to the second embodiment 200.

Figure 11A:
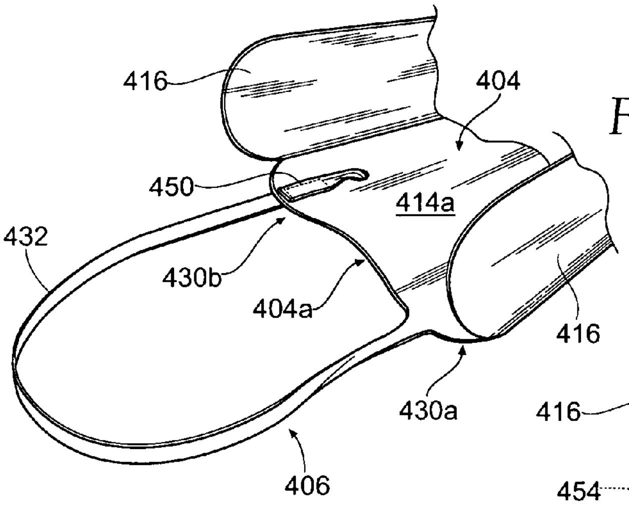
FIG. 11A is a perspective view of a fourth preferred embodiment of a retainer mechanism according to the present invention.
Figure 11B:
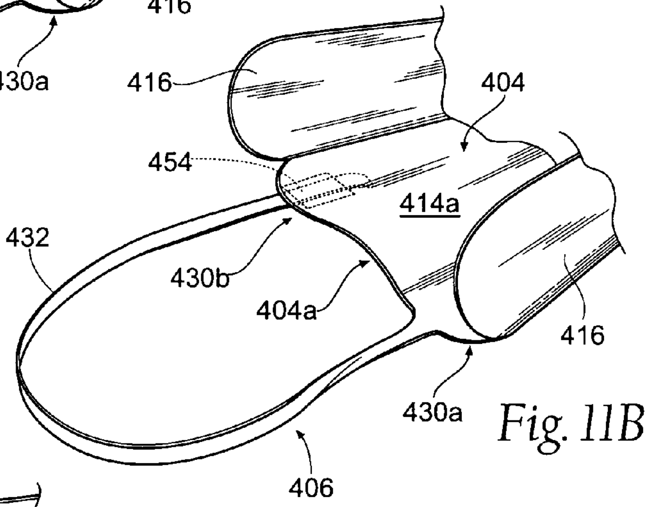
FIG. 11B is a perspective view of a fifth preferred embodiment of a retainer mechanism according to the present invention.
Figure 11C:
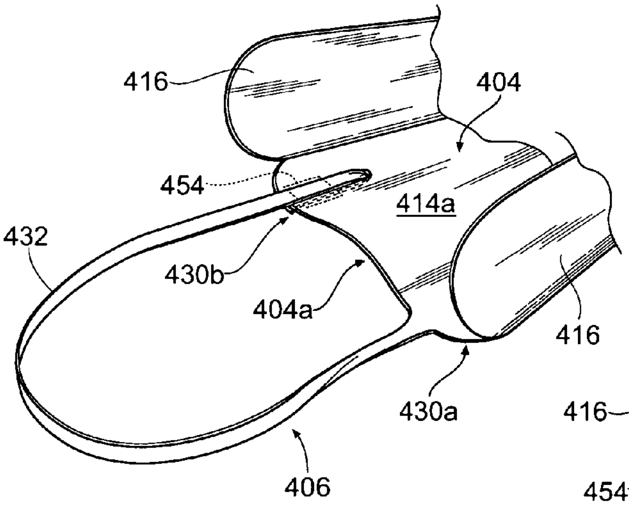
FIG. 11C is a perspective view of a sixth preferred embodiment of a retainer mechanism according to the present invention.
Figure 11D:
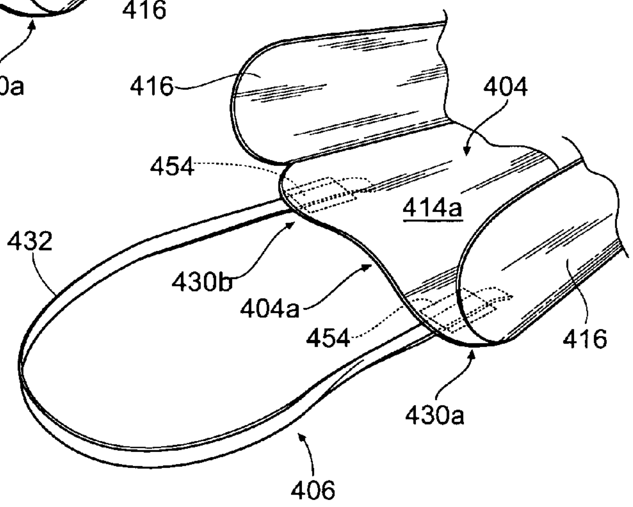
FIG. 11D is a perspective view of a seventh preferred embodiment of a retainer mechanism according to the present invention.

FIGS. 11A-11H provide examples of different retainers 406 that may be incorporated into an emesis container according to the present invention. FIGS. 11A-11D provide examples of a retainer 406 comprising a strap 432 coupled to a first retainer site 430*a* on the right side of the back panel 414 of the chute portion 404 and coupled to a second retainer site 430*b* on the left side of the back panel 414 of the chute portion 404. Coupling at preferably one of the sites 430*a*,430*b*, may be accomplished by having one end of the strap 432 integrally formed as a part of the unitary member, an example of which can be seen in FIGS. 11A-11C. If an end of the retainer 406 is to be formed integrally with or otherwise relatively permanently attached to the unitary member, while it could be provided on either side, it may be preferable to do so on at the right-hand retainer site 430*a*, as it is common for patients to be accessible primarily from their anatomical left side, such as when a patient is loaded into an ambulance. The strap 432 may be provided with an adhesive patch 450, which is activated and then secured to the strap 432 itself, or to the chute portion 404, as seen in FIG. 11A. Alternatively, or additionally, the back panel 414 of the chute portion 404 may be provided with one or more adhesive patches 454 to which the strap 432 may be adhered, as seen in FIGS. 11B-11D.

Figure 11E:
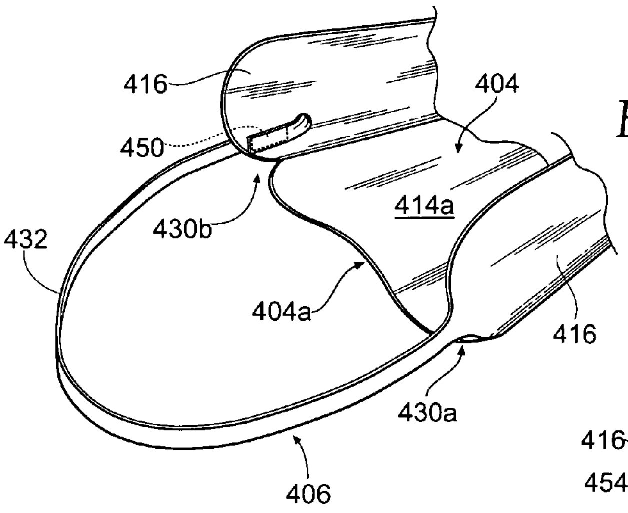
FIG. 11E is a perspective view of a eighth preferred embodiment of a retainer mechanism according to the present invention.
Figure 11F:
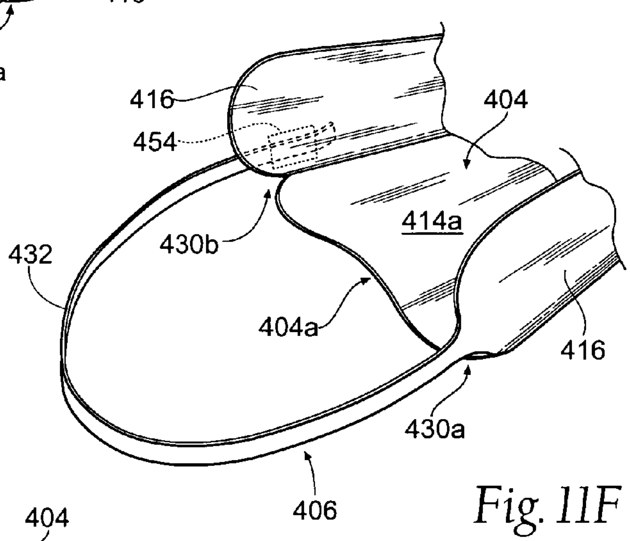
FIG. 11F is a perspective view of a ninth preferred embodiment of a retainer mechanism according to the present invention.
Figure 11G:
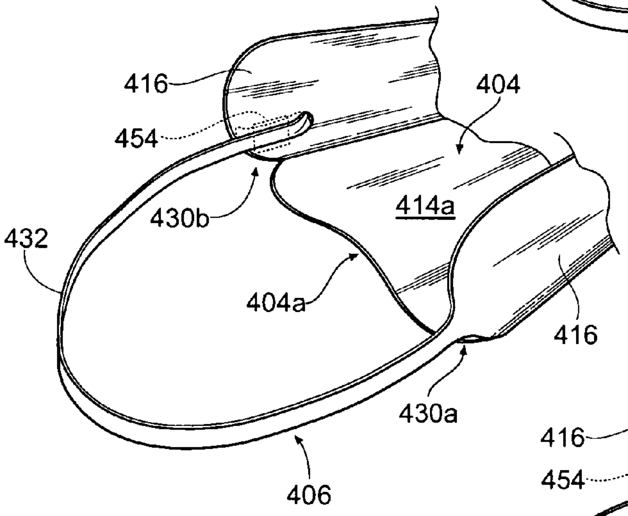
FIG. 11G is a perspective view of a tenth preferred embodiment of a retainer mechanism according to the present invention.

FIGS. 11E-11H provide examples of a retainer 406 comprising a strap 432 coupled to a first retainer site 430*a* on the right side panel 416 of the chute portion 404 and coupled to a second retainer site 430*b* on the left side panel 416 of the chute portion 404. Coupling at preferably one of the sites 430*a*, 430*b*, may be accomplished by having one end of the strap 432 integrally formed as a part of the unitary member, an example of which can be seen in FIGS. 11E-11G. The strap 432 may be provided with an adhesive patch 450, which is activated and then secured to the strap 432 itself, or to the chute portion 404, as seen in FIG. 11E. Alternatively, or additionally, one or more of the side panels 416 of the chute portion 404 may be provided with an adhesive patch 454 to which the strap 432 may be adhered, an example of which can be seen in FIGS. 11F-11H.

Figure 11H:
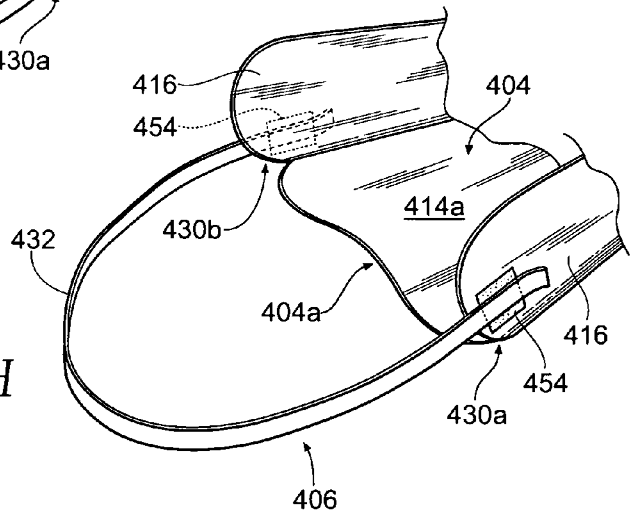
FIG. 11H is a perspective view of a eleventh preferred embodiment of a retainer mechanism according to the present invention.

FIG. 11D and FIG. 11H provide an alternate retainer 406 comprising a strap 432 provided separately from the unitary member and then coupled to the member at two retainer sites 430. The retainer sites 430 could be provided anywhere preferably on the chute portion 404, but more preferably on the side panels 416 thereof. Such coupling may be provided by, for example, an adhesive patch 454 may be affixed to the chute portion 404, preferably on the side panels 416 near the entrance end 404*a* of the chute 404.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An emesis container comprising:

a unitary member including a. a receptacle portion having an open end and a closed end, the open end having a perimeter; and b. a chute portion having an entrance end and an exit end oppositely disposed the entrance end, the exit end being coupled to the receptacle proximate the open end, wherein the chute portion comprises:

b1. a back panel having a front surface and a back surface, the back panel extending between and including the entrance end and the exit end; and b2. two side panels extending away from the back panel front surface, the side panels extending between and including the entrance end and the exit end, the side panels having a first edge portion at the entrance end, a second edge portion directly coupled to the back panel, and a third edge portion disposed opposite the second edge portion, the third edge portion extending from the receptacle open end towards the entrance end;

wherein the first edge portion and the third edge portion are non-colinear and the first edge portion connects the third edge portion to the second edge portion, wherein the back panel and side panels extend around less than the bag open end perimeter.

2. An emesis container according to claim 1, the container further comprising a retainer coupled to the chute portion at at least one retainer site.

3. An emesis container according to claim 2, the retainer being coupled to the chute portion by being integrally formed with the chute portion at at least one retainer site.

4. An emesis container according to claim 2, at least one of the retainer sites comprising a patch of adhesive affixed to the chute portion.

5. An emesis container according to claim 2, wherein the retainer is a strap.

6. An emesis container according to claim 5, wherein the strap is formed from the same material as the chute portion.

7. An emesis container according to claim 5, the strap including an adhesive patch covered by a releasable liner.

8. An emesis container according to claim 2, wherein at least one retainer site includes a stress riser.

9. An emesis container according to claim 2, wherein at least one retainer site comprises an aperture formed in the chute portion.

10. An emesis container according to claim 1, further comprising at least one reinforcement member coupled to the unitary member.

11. An emesis container according to claim 10, at least one reinforcement member being adapted to maintain the open end of the receptacle portion in a substantially open configuration regardless of the amount of liquid present in the receptacle portion.

12. An emesis container according to claim 10, wherein at least one reinforcement member is coupled to an outer surface of the receptacle portion.

13. An emesis container according to claim 10, wherein at least one reinforcement member is coupled to the unitary member closer to the receptacle portion open end than to the receptacle portion closed end.

14. An emesis container according to claim 10, wherein at least one reinforcement member is plastically deformable.

15. An emesis container according to claim 14, wherein at least one plastically deformable reinforcement member is a metal wire.

16. An emesis container according to claim 10, wherein at least one reinforcement member is a cuff provided along at least a portion of the open end perimeter of the receptacle portion.

17. An emesis container according to claim 1, wherein the receptacle portion comprises a flexible material.

18. An emesis container according to claim 17, wherein the flexible material comprises plastic.

19. An emesis container according to claim 18, wherein the plastic comprises polyethylene.

20. An emesis container according to claim 17, wherein the flexible material has a thickness of five mils.

21. An emesis container according to claim 1, wherein the receptacle portion is translucent.

22. An emesis container according to claim 1, the receptacle portion further including volume demarcations.

23. An emesis container according to claim 1, the receptacle portion having a liquid capacity of at least 1200 milliliters.

24. An emesis container according to claim 23, the receptacle portion having a liquid capacity of 2500 milliliters.

25. An emesis container according to claim 1, wherein the open end perimeter encompasses at least thirty square inches.

26. An emesis container according to claim 1, wherein the back panel front surface has an area of at least thirty-six square inches.

27. An emesis container according to claim 3, the retainer being coupled to the chute portion by being integrally formed with the chute portion back panel at at least one retainer site.

28. An emesis container according to claim 3, the retainer being coupled to the chute portion by being integrally formed with one of the side panels at at least one retainer site.

29. An emesis container according to claim 4, the patch of adhesive affixed to the back panel.

30. An emesis container according to claim 4, the patch of adhesive affixed to one of the side panels.

* * * * *